(12) United States Patent
Roundhill et al.

(10) Patent No.: US 8,094,893 B2
(45) Date of Patent: Jan. 10, 2012

(54) SEGMENTATION TOOL FOR IDENTIFYING FLOW REGIONS IN AN IMAGE SYSTEM

(75) Inventors: David N. Roundhill, Woodinville, WA (US); Roy B. Peterson, Seattle, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1252 days.

(21) Appl. No.: 10/536,642

(22) PCT Filed: Nov. 13, 2003

(86) PCT No.: PCT/IB03/05306
§ 371 (c)(1),
(2), (4) Date: May 27, 2005

(87) PCT Pub. No.: WO2004/051310
PCT Pub. Date: Jun. 17, 2004

(65) Prior Publication Data
US 2006/0098853 A1 May 11, 2006

Related U.S. Application Data

(60) Provisional application No. 60/430,226, filed on Dec. 2, 2002.

(51) Int. Cl.
*G06K 9/00* (2006.01)
(52) U.S. Cl. ........ 382/128; 600/443; 600/453; 600/454; 600/407
(58) Field of Classification Search ............... 382/128; 600/441, 443, 453–456
See application file for complete search history.

(56) References Cited

U.S. PATENT DOCUMENTS

| | | | | |
|---|---|---|---|---|
| 5,190,044 A | * | 3/1993 | Kawasaki et al. | 600/455 |
| 5,197,477 A | * | 3/1993 | Peterson et al. | 600/454 |
| 5,365,929 A | | 11/1994 | Peterson | |
| 5,390,677 A | * | 2/1995 | Ferrera et al. | 600/455 |
| 5,601,084 A | * | 2/1997 | Sheehan et al. | 600/450 |
| 5,840,032 A | * | 11/1998 | Hatfield et al. | 600/443 |
| 5,904,653 A | * | 5/1999 | Hatfield et al. | 600/454 |
| 5,910,118 A | * | 6/1999 | Kanda et al. | 600/455 |
| 5,913,824 A | * | 6/1999 | Ogasawara et al. | 600/455 |
| 5,957,138 A | * | 9/1999 | Lin et al. | 600/453 |
| 6,042,545 A | * | 3/2000 | Hossack et al. | 600/443 |

(Continued)

FOREIGN PATENT DOCUMENTS

EP 0 885 594 12/1998

OTHER PUBLICATIONS

Hein, I.A. O'Brien, W.D., Jr., "Current time-domain methods for assessing tissue motion by analysisfrom reflected ultrasound echoes-a review", IEEE Transactions on Ultrasonics, Ferroelectrics and Frequency Control, IEEE, Publication Date: vol. 40 No. 2, Mar. 1993, pp. 84-102.*

(Continued)

*Primary Examiner* — Samir Ahmed
*Assistant Examiner* — Mek Bekele

(57) ABSTRACT

An ultrasound system and method that identify flow regions within a volume. The system comprises: a survey system for collecting motion data from a target image; a segmentation system for mapping a region of flow within the image based on the motion data; and a flow acquisition system that automatically limits the collection of flow image data within the image to the region of flow.

19 Claims, 3 Drawing Sheets

U.S. PATENT DOCUMENTS

| | | | |
|---|---|---|---|
| 6,106,466 A * | 8/2000 | Sheehan et al. | 600/443 |
| 6,139,501 A | 10/2000 | Roundhill et al. | |
| 6,196,971 B1 | 3/2001 | Friedman et al. | |
| 6,210,334 B1 * | 4/2001 | Phillips | 600/453 |
| 6,296,612 B1 * | 10/2001 | Mo et al. | 600/455 |
| 6,447,453 B1 | 9/2002 | Roundhill et al. | |
| 6,450,961 B1 * | 9/2002 | Shiki et al. | 600/458 |
| 6,458,083 B1 * | 10/2002 | Jago et al. | 600/443 |
| 6,471,650 B2 | 10/2002 | Powers et al. | |
| 6,475,149 B1 * | 11/2002 | Sumanaweera | 600/441 |
| 6,491,636 B2 * | 12/2002 | Chenal et al. | 600/450 |
| 6,500,125 B1 * | 12/2002 | Muzilla et al. | 600/454 |
| 6,537,221 B2 * | 3/2003 | Criton et al. | 600/454 |
| 6,656,121 B2 * | 12/2003 | Jeong et al. | 600/443 |
| 6,685,643 B1 * | 2/2004 | Waldinger et al. | 600/444 |
| 6,813,512 B2 * | 11/2004 | Aldefeld et al. | 600/410 |
| 6,836,557 B2 * | 12/2004 | Tamez-Pena et al. | 382/128 |
| 7,101,336 B2 * | 9/2006 | Miller | 600/443 |
| 2002/0077546 A1 * | 6/2002 | Aldefeld et al. | 600/424 |
| 2002/0159951 A1 * | 10/2002 | Unger et al. | 424/9.51 |
| 2006/0074309 A1 * | 4/2006 | Bonnefous | 600/437 |

OTHER PUBLICATIONS

Wilhjelm et al., "Quantitative Analysis of Ultrasound B-Mode Images of Carotid Atherosclerotic Plaque: Correlation with Visual Classification and Histological Examination", published on Dec. 1998, IEEE in transactions in medical imaging, vol. 17 No. 6, pp. 910-922.*

* cited by examiner

SEGMENTATION TOOL FOR IDENTIFYING FLOW REGIONS IN AN IMAGE SYSTEM

CROSS REFERENCE TO RELATED CASES

Applicants claim the benefit of Provisional Application Ser. No. 60/430,226, filed Dec 2, 2002.

The present invention relates generally to ultrasound imaging systems, and more particularly relates to a system and method for optimizing an ultrasound imaging process.

Thanks to an ongoing series of technological advances, diagnostic ultrasound remains one of today's most important medical tools. Since the mid-1960's, continuous advances have improved the clinical value of ultrasound, expanding its capabilities, accuracy, and ease of use. Recent advances, such as real-time 3D imaging can be used to collect important details, such as blood flow and other motion data, during a relatively short exam. This type of data is particularly useful in areas such as cardiology, where an abnormality in the flow of blood throughout the heart may be an indicator of heart disease.

Unfortunately, because ultrasound data is collected using sound waves, it is subject to the physical limitations of the speed of sound in tissue. Specifically, ultrasound data is acquired with a transducer that transmits an acoustic pulse along a look direction or line, and then listens for echoes along the same line. Received echo information gathered from a set of adjacent lines can be processed and used, for instance, to form an image that can be displayed on a monitor. Depending on the particular implementation, the number and density of the lines will vary. In the case of a two-dimensional (2D) image the lines form a frame, and in the case of a three-dimensional (3D) image the lines form a volume. Because ultrasound information is typically displayed in real-time as a series of frames or volumes, the time it takes to form an image (i.e., frame or volume) is critical for many applications. Specifically, if the time is too great, the frame rate or volume rate may be too slow for ultrasound imaging of moving tissue (for example, blood or fetal anatomy).

Color flow Doppler, which generates a color image that indicates velocity and direction of any flow within an image, is particularly susceptible to the above-mentioned problems. Motion is detected by analyzing differences in the received echo signal for multiple received echo lines formed along the same axis. This type of data can provide important analytical information, including blood flow velocity, regurgitation, etc. However, since the detection of flow along each look line requires the use of multiple transmit/receive cycles, the use of color flow Doppler significantly increases the time it takes to form an image, and thereby further reduces the frame or image rate. As such, the acquisition of color flow Doppler data throughout an entire image volume is not practical in many clinical contexts because of the substantial degradation in the acquisition rate due to the number of transmit/receive cycles required to obtain Doppler phase shift information.

If the flame rate is too slow the resulting ultrasound image may misrepresent the physiological condition by introducing imaging artifacts and distortions. Accordingly, for some applications involving color flow Doppler, such as analyzing regurgitent flow through the mitral valve of the heart, the side effects of an inadequate image rate may limit the diagnostic performance of the ultrasound imager.

Another proposed application for ultrasound that is also adversely affected by the physical limitation of the speed of sound in tissue is the acquisition of data for subsequent off-line or retrospective analysis. In this scenario, sufficient ultrasound data is acquired from a region within the patient so that a subsequent diagnosis may be made from that data. The benefits of such an approach are several-fold. In one case, the attending clinician need only locate the general region of interest, such as the patient's heart, from which to acquire ultrasound data. With the use of an ultrasound scanner capable of acquiring data from a 3D volume, the clinician performing the diagnosis may then navigate through the acquired data to obtain the specific components of the data required to form a diagnosis. In this fashion, the time required to acquire data from the patient is minimized by allowing the diagnosis to take place after the exam, rather than during the exam. This approach allows the diagnosing clinician to perform their diagnostic function both at a different time and a different location from the examination of the patient. Furthermore it is possible to employ an attending clinician with a lesser skill set than would be required were the diagnosis to be performed during the exam. The use of this approach requires that all the data required to form a diagnosis be acquired during the exam.

One important component of many exams is the acquisition of flow data from potentially diseased portions of the anatomy being imaged. Detection of such a region may be accomplished using an algorithm within the ultrasound scanner that detects blood flow conditions that correspond to the anatomy and physiology of interest. An example of this is the common finding of mitral valve regurgitation that has a common color flow Doppler signature. Once such a region has been identified using such an ultrasound scanner based algorithm, the ultrasound scanner can automatically be made to perform a specialized acquisition such as continuous (CW) or pulsed wave (PW) Doppler.

This application, which has been proposed in the field of cardiology, seeks to obtain spectral Doppler data and gray-scale echo data from a patient's heart in a short period of time (e.g., several heart cycles), and then store the data for later analysis. Such a system would capture data from all relevant regions of interest, such as blood flow velocity at the mitral valve. Because a physician would not view the information until a later time, the examination time could be greatly reduced. Unfortunately, the application of spectral Doppler to collect data for an entire volume is impractical since, for instance, the placement of the Doppler sample volume (i.e. the point at which the Doppler data is acquired) is highly specific.

One solution is to allow the technician to selectively identify the placement of the Doppler sample volume at various points of interest, and then collect data from only those points. However, such a process is limited to the technician's ability to accurately place the Doppler sample volume. If the technician fails to precisely capture the point of interest, the results would not be known until a later time when an off-line analysis took place, and the test would have to be rescheduled.

Nonetheless, significant potential benefits exist for advanced ultrasound techniques such as real-time color flow Doppler and spectral Doppler. However, until the above-mentioned limitations are addressed, the use of advanced ultrasound techniques will be restricted.

The present invention addresses the above-mentioned problems, as well as others, by providing an ultrasound system that automatically identifies regions of interest, namely those that include tissue motion or blood flow. Once the region of interest is identified, an advanced ultrasound modality, such as color flow Doppler or spectral Doppler can be effectively applied to the region of interest to achieve a desired result.

In a first aspect, the invention provides a method a method of capturing an image using an ultrasound system, comprising: surveying the image to collect motion data; analyzing the motion data to identify a flow in the image; and scanning a limited region of the image containing the flow with a flow imaging technique.

In a second aspect, the invention provides an ultrasound system, comprising: a survey system for collecting motion data from a target image; a segmentation system for mapping a region of flow within the image based on the motion data; and a flow acquisition system that automatically limits the collection of flow image data within the image to the region of flow.

In a third aspect, the invention provides an ultrasound system that includes a segmentation tool for segmenting an image into a flow and a non-flow region, comprising: a system for performing a survey of the image, wherein the survey collects a sample of motion data; and a system that analyzes the sample of motion data to separately identify the flow region and the non-flow region within the image.

In a fourth aspect, the invention provides a program product stored on a recordable medium for optimizing ultrasound data, comprising: means for receiving survey data representative of motion in a volume of ultrasound data; means for mapping the survey data into a motion map that indicates flow and non-flow regions; and means for limiting the collection of flow data to the flow regions.

In a fifth aspect, the invention provides an ultrasound method for performing a retrospective analysis, comprising: surveying an image to identify a point of interest; obtaining an acquisition volume of spectral data from the image, wherein the acquisition volume includes at least one sample volume encompassing the point of interest; saving the spectral data from the acquisition volume, wherein the spectral data includes phase information; and retrospectively analyzing the saved spectral data.

These and other features of this invention will be more readily understood from the following detailed description of the various aspects of the invention taken in conjunction with the accompanying drawings in which.

SYSTEM OVERVIEW

Figure 1:
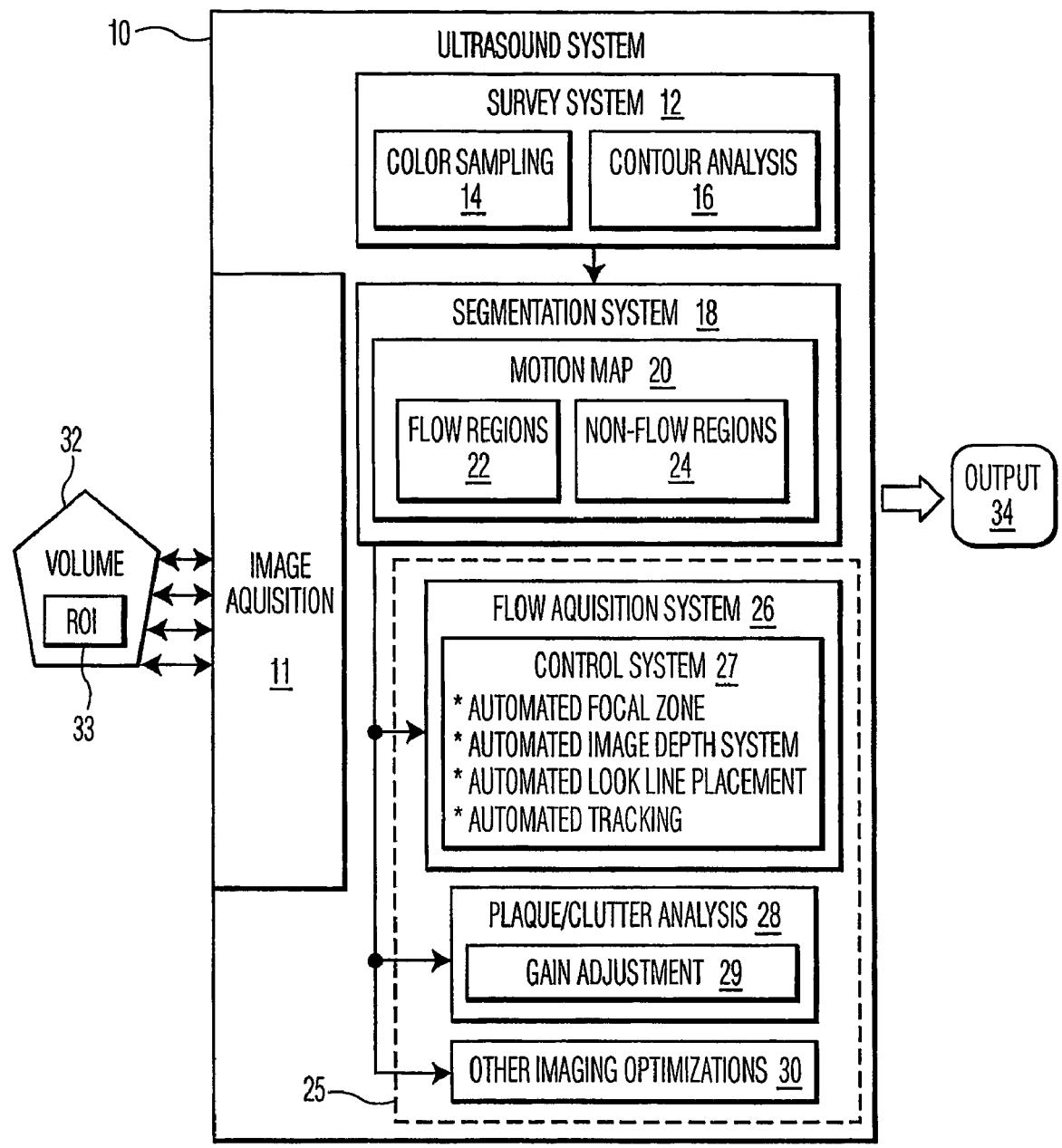
FIG. 1 depicts an ultrasound system in accordance with the present invention.

Referring now to the drawings, FIG. 1 depicts an ultrasound system 10 for imaging a target volume 32, and more specifically allows for the application of an ultrasound modality to a region of interest (ROI) 33 in the target volume 32. In the embodiments described herein, the applications generally provide some type of "flow" imaging for collecting color flow data, and include color flow Doppler and spectral Doppler. However, any other type of ultrasound modality could likewise be utilized, e.g., B-FLOW™, time domain correlation, speckle tracking, strain imaging, other Doppler techniques etc., and can be implemented in manners not described herein. It should be understood that the present invention uses the term "flow" to describe any type of movement, including blood flow, tissue motion, target motion, etc., and the specific use of such terms herein are not intended to limit the scope of the invention.

The present invention facilitates the use of ultrasound modalities, including spectral Doppler and color flow Doppler, by first segmenting the target volume 32 into flow and non-flow regions. To achieve this, ultrasound system 10 is provided with a survey system 12, a segmentation system 18, and one or more applications 20. Ultrasound system 10 acquires ultrasound data from image 32 using an imaging acquisition system 11. Imaging acquisition system 11 may include any mechanisms known in the art for collecting and processing ultrasound data, such as one or more transducers, related hardware, software, input devices, monitor, etc. In addition, ultrasound system may create an output 34. Output 34 may include, for instance, a stream of images that can be viewed in real-time, an electronic/digital file for storing image data that, e.g., allows a physician to retrospectively study the scanned image, etc. Images may be collected and/or processed as a 2D slice (i.e., frame) or a 3D volume, and the concepts described herein are applicable to both.

As noted above, it is often the case that a target volume 32 being scanned will have one or more specific regions of interest 33, e.g., the mitral valve in the heart, the wall of the aorta, some other important vascularity, a point, etc. However, given the limitations mentioned above, it may be impractical to scan the entire volume 32 using an imaging technique such as color flow Doppler or spectral Doppler. Because the region of interest 33 typically involves some motion or flow, the present invention automatically segments the flow region(s) from the non-flow region(s). The regions may be segmented in any shape or volume, including, but not limited to, a 3D pie slice, a cube, an arbitrary shape, a collection of shapes, etc. Once the flow region is identified, a flow imaging technique can be restrictively applied to the regions of interest.

To implement the above, ultrasound system 10 of the present invention includes a survey system 12 that "surveys" the volume to collect motion data. Survey system 12 can be implemented in any manner to collect any type of "survey" data that can help indicate a region of interest 33, namely, motion or flow. Once identified, a segmentation system 18 may be implemented to store the information in a motion map 20 that delineates the flow regions 22 from the non-flow regions 24. This information can then be used by one or more applications 25, as described in further detail below. While the present invention is generally described in terms of identifying motion or flow, the invention may be implemented in terms of detecting the absence of motion or flow, and such an embodiment is believed to fall within the scope of the invention.

Real-time Flow Imaging

Figure 2:
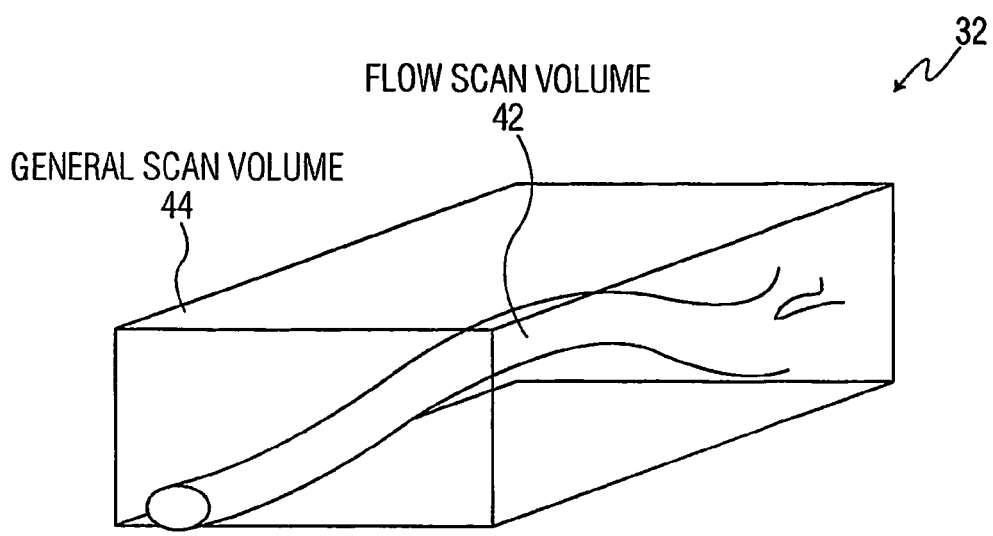
FIG. 2 depicts a volume containing a vessel having a flow and non-flow region.

As noted above, the ability to effectively collect and display real-time flow imaging data, such as color flow Doppler data, is limited by a minimum acquisition frame or volume rate (e.g., 15-100 Hz) needed to adequately sample the physiology. However, such a required rate of acquisition may be unachievable if an entire image is scanned using flow imaging. For instance, consider the volume 32 depicted in FIG. 2. Volume 32 generally comprises a flow region 42, and a non-flow region 44. The flow region 42 comprises a vessel, e.g., a carotid artery, while the non-flow region comprises, e.g., muscle, fat, connective tissue, etc. If the entire image were scanned using color flow Doppler, which requires an ensemble of transmit/receive cycles (e.g., 5-12) for each line, an effective frame rate could not be maintained and aliasing errors and the like could be introduced into the display. Thus, accurate information regarding the velocity and direction of the blood flow through the vessel could not be obtained.

To overcome this, the present invention first segments the image into flow and non-flow regions, and then limits the use of flow imaging to the flow regions, i.e., a region of interest. Using the ultrasound system 10 depicted in FIG. 1, survey system 12 is first applied to collect "motion" data to help indicate motion or flow. It should be recognized that any type of data indicative of motion could be collected. In one exemplary embodiment, a color flow Doppler sampling system 14 is provided that collects color flow data from the entire volume 32 at some predetermined time interval, e.g., every nth frame. In another exemplary embodiment, a contour analysis system 16 may be implemented to identify a feature (e.g., a mitral valve) around or through which flow or motion is typical. U.S. Pat. No. 6,447,453, which is hereby incorporated by reference, discloses such a system. In this case, the motion data may comprise one or more identified contours or patterns within the image.

Once collected, the motion data is analyzed by segmentation system 18 to specifically identify which regions within volume 32 contain flow. The presence of flow can be identified in any known manner. For instance, conventional color flow techniques can be used to determine velocities within an image, and a velocity threshold can be established that separates flow from non-flow regions. Alternatively, the power of an image signal can be analyzed to identify a flow, and a power threshold can be established that separates flow from non-flow regions. Further, in the case of a contour analysis system 16, segmentation system 18 may include a pattern recognition system. Thus, certain identified contours can be recognized as being associated with flow, while others can be recognized as being associated with non-flow.

Segmentation system 18 may generate a motion map 20 in the form of a 2D frame or 3D volume that indicates flow regions 22 and non-flow regions 24. This motion map 20 can then be utilized by various applications 25. In this exemplary application, the motion map can be utilized by the flow imaging acquisition system 26 to restrict flow imaging to the identified region(s) of interest 33 within the volume 32. The non-flow portion of the image can be scanned with standard grayscale imaging.

In one exemplary embodiment, flow acquisition system 26 may include a control system 27 that tells the image acquisition system 11 to use color flow Doppler scanning only for the region(s) of interest 33 within image 32 and grayscale for the non-flow regions. Control system 27 may, for example, comprise a system for automatically setting a focal zone position based on the color flow data and a system for automatically setting an image depth based upon the location of a peak motion signal within the color data to limit the collection of high-density data to the region of interest 33. While this embodiment is described with reference to color flow Doppler scanning, any imaging technique may be utilized, e.g., color, B-FLOW, power motion imaging, tissue Doppler imaging, pulse wave, continuous wave, etc. Because flow data collection is limited to a relatively small region of interest 33, real-time 2D or 3D color imaging for that specific region can be effectively achieved, (i.e., an adequate acquisition rate can be maintained).

Flow acquisition system 26 can adjust a set of acquisition parameters to effectively scan the region of interest 33. Such parameters may include, e.g., b-mode line densities, color flow line densities, pulse repetition frequency, and ensemble length.

As is evident, survey system 12 is only concerned with detecting the presence of motion, as opposed to, e.g., making an accurate estimate of velocity. In one embodiment, survey system could be implemented utilizing: (1) a relatively low sampling of the spatial frequencies present in the image 32; (2) a relatively low density of scan lines (i.e., lines per millimeter or degree) relative to what would be typical to form an image; and/or (3) a lower than normal ensemble or number of transmit/receive cycles per line (e.g., 2 or 3). Accordingly, survey system 12 may generally utilize a relatively non-quantitative analysis, whose properties would potentially be inadequate for clinical flow imaging.

Alternatively, survey system 12 could utilize a very high spatial density scan and/or high sensitivity scan as a means for collecting motion data. While such a process would take additional time, it would only need to be done once (or relatively infrequently) to accurately capture the flow fields within an image.

Control system 27 may also include a tracking system that allows the survey system 18 to automatically re-survey the image every so often in a continuous mode to account for movement of the thing being imaged, movement of the transducer, etc. Thus, real-time adjustments could be made, e.g., every nth frame, to ensure proper tracking of the flow and non-flow regions. Alternatively, a one-button push system could be utilized to allow the technician to manually decide when motion data was to be collected.

Furthermore, once the target volume 32 has been segmented, further imaging may be applied more specifically to, for example, image the general non-flow region with standard b-mode scanning and the vascular flow region with targeted color flow. The net result of this approach is a substantial improvement in frame rate. Additionally, the viewable image benefits from reduced transmission of unnecessary flow pulses and the user benefits from an automatic isolation of the flow region.

A further application for using the segmented data may comprise a plaque/clutter analysis system 28 that automatically adjusts the gain of the imaging acquisition system 11. In imaging vessels with some low level echoes, it would be advantageous to determine whether such echoes stem from soft plaque, or from clutter (i.e., reverb). If the echoes stem from plaque, it would be useful to automatically increase the 2D gain to make the plaque more visible. On the other hand, if the low level echoes stem from clutter, it would be useful to automatically reduce the overall gain. Using only gray-scale data, it is difficult to determine the nature of these low level echoes.

To address this, the present invention provides a plaque/clutter analysis system 28. For distinguishing plaque from clutter when low level echoes are present in vessel interiors, the motion signals present in the same locations as the low level echoes can be analyzed. If there is no flow signal, the low level echoes are likely to be plaque, and an increase in gain is implemented to highlight those echoes. Alternately, if flow is present where the low level echoes exist, the echoes are likely to be clutter or reverb, and a reduction in gain is then automatically propagated to achieve automatic clutter suppression.

Furthermore, the segmented data may be utilized by any other imaging optimizations 30. For instance, in areas like vascular imaging, where the object of interest is a vessel whose interior is anechoic, ultrasound systems tend to key off the surrounding musculature. This means that, while the muscle layers become appropriately gained, the walls of the vessels become either over-gained or under-gained. Furthermore, in over-gained situations, clutter is introduced into the lumen. The sonographer typically does not care about the presentation of the musculature but focuses only on the vessel walls and interior. In this instance, the map 20 can be used to define a tight region of interest, centered around the vessel, on the regular 2D frame that may be input to an optimization algorithm. When the optimization works on this tight region, echoes from outside muscle layers beyond the vessels can be excluded, hence reducing the instances where the bright or dark echoes from the musculature inappropriately influence the optimization of the 2D echoes in the vessel walls and interior.

Retrospective Analysis

As noted above, an important potential application of retrospective analysis involves fields such as cardiology, where the challenge is to accurately acquire data, such as spectral Doppler data around the valves of the heart. As noted above, in order to retrospectively analyze collected spectral Doppler data, it is critical that the sample volume be placed at a point of interest so that the data of interest can be accurately and precisely captured, e.g., a typical Doppler sample volume is 1 mm in diameter and 3 mm long. This process is typically done during a lengthy exam, because the placement of the sample volume is specific to the valve being studied and is also specific to the patient An exemplary embodiment of an application utilizing retrospective analysis is further described with reference to FIGS. 3-5, which depict a scan of a heart 40 within a 3D volume 62.

The present invention utilizes the concepts described above to automatically implement the process of collecting a sample volume of spectral Doppler data for retrospective analysis. To achieve this, survey system 12 of ultrasound system 10 is utilized to collect motion data. Once collected, segmentation system 18 can specifically identify and map flow locations, namely, the point of interest. Finally, the flow acquisition system 26 can be utilized to obtain a sample volume containing spectral Doppler data at the point of interest, which can be stored for later analysis.

Figure 3:
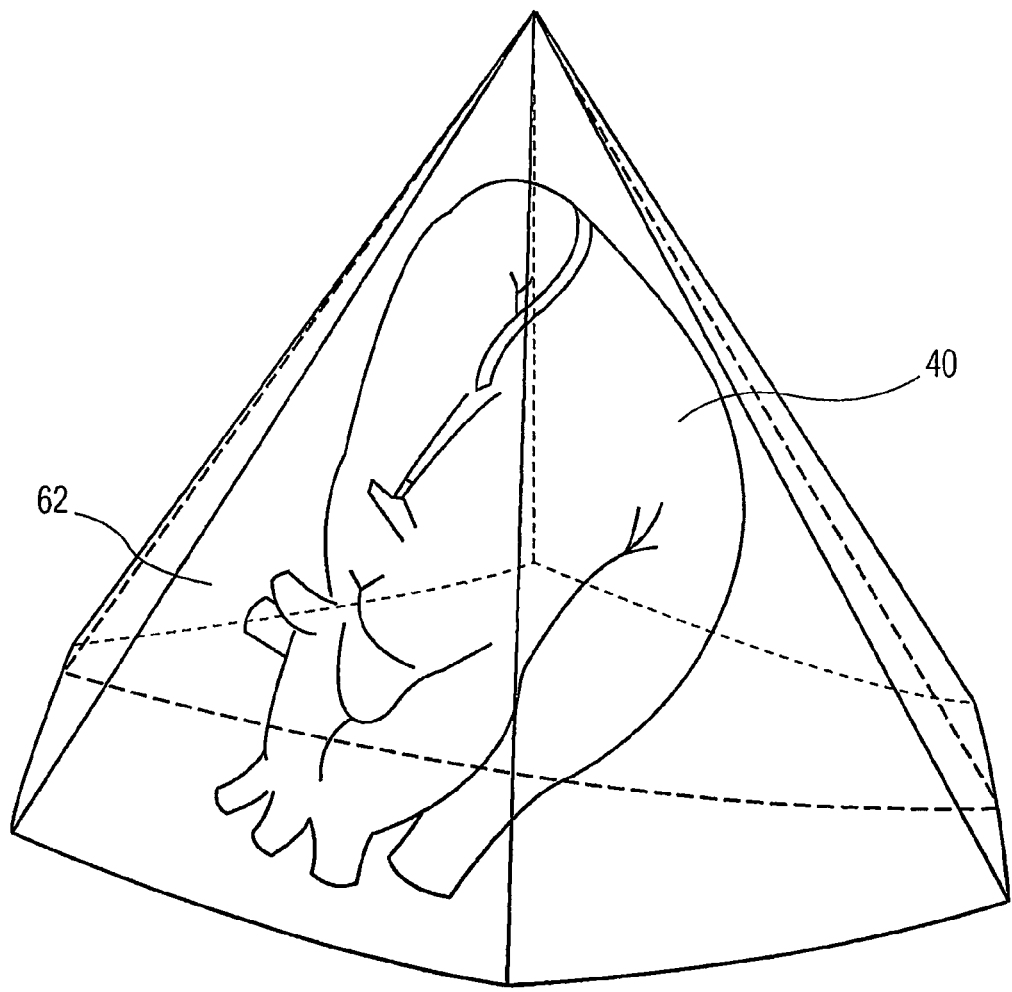
FIG. 3 depicts a volume containing a heart.

In one embodiment of the invention, based on the identification of a point of interest, the look direction in the volume acquisition is determined automatically and spectral Doppler data is acquired axially along that look direction at multiple ranges. In addition, the use of multi-line beamforming to provide multiple look directions, either around the same point or potentially at arbitrary look directions may also be incorporated. To demonstrate this technique, FIG. 3 shows a heart 40 imaged as a volume 62 using real time ultrasound imaging.

Typically, a technician acquires a series of 2D images from various perspectives to help reconstruct in their mind a 3D view. The goal for 3D is the full acquisition of a sample volume in a relatively short time. However, there is no equivalent of 3D for spectral Doppler, which continues to be an important part of an ultrasound exam in cases where high flow sensitivity and temporal resolution are required. Because spectral Doppler consists of interrogating (essentially) a point in space, skill and time are required by the technician to obtain specific data. The present invention addresses this by automatically acquiring an "acquisition volume" of spectral Doppler data (including phase information) that covers a larger region than a single point of interest. This allows the technician to be less sildlful, and still capture the point of interest within the acquisition volume. Then, retrospectively, either the technician or control system 27 can identify the sample volume within the acquisition volume and generate spectral Doppler for the sample volume of interest One method for achieving this involves capturing the received data from several "range gates" and analyzing each one independently to derive the associated spectral data. Such a methodology is described in U.S. Pat. No. 5,365,929, which is hereby incorporated by reference. Because the exact range/depth of the sample volume for which the spectral data is desired is uncertain, data is captured over a wider range than would otherwise be normal. The actual sample volume can later be defined retrospectively.

In order to determine the proper look direction, the region of interest, e.g., a valve, must be automatically identified. One method of identifying a valve is to use survey system 12 to identify motion data as an area of high velocity flow. This can be achieved with a 3D color Doppler image that would generate a motion map 20 to indicate where flow was occurring. Another method, described above with reference to U.S. Pat. No. 6,447,453, utilizes a contour analysis system to identify motion data, e.g., using pattern recognition to detect a mitral valve. Once identified, the look direction and range of the scan line can be automatically determined by control system 27.

Figure 4:
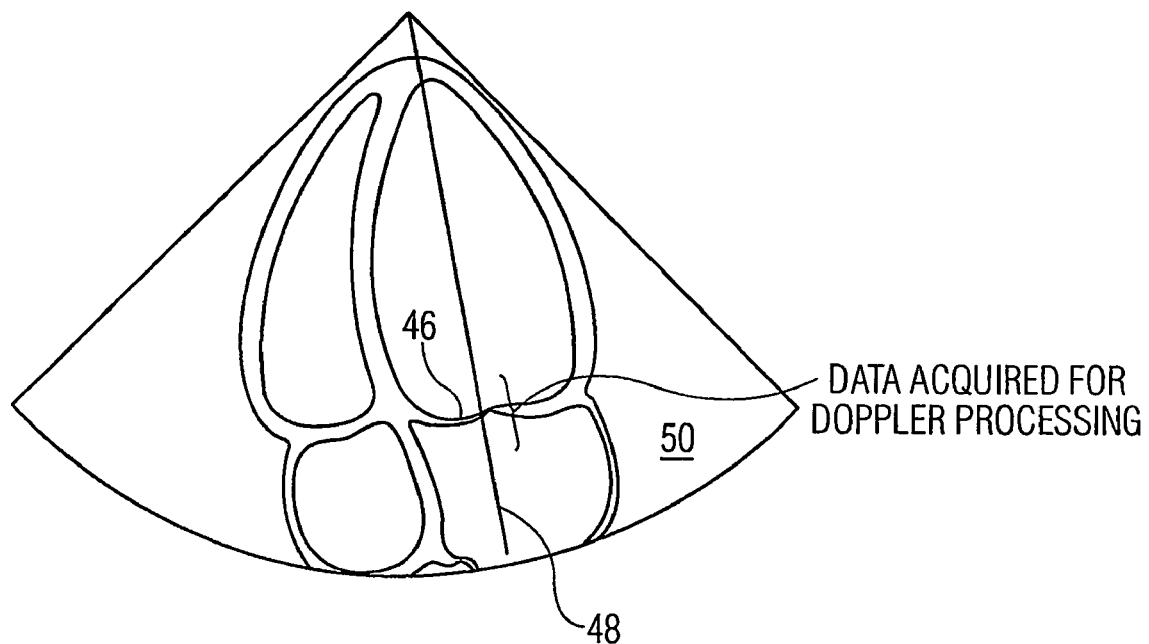
FIG. 4 depicts a volume containing a heart wherein the mitral valve has been automatically detected and imaged with a scan line in accordance with the present invention.

FIG. 4 shows a mitral valve 46 with a line of acquisition 48 placed automatically. Note that in this case, data is acquired for an acquisition volume 50 that includes the left ventricle and the left atrium to ensure that sufficient data is available for retrospective analysis. Note also that as the heart moves as a function of the heart cycle, the location of the Doppler imaging line of sight can be repositioned automatically by the tracking feature of control system 27.

Figure 5:
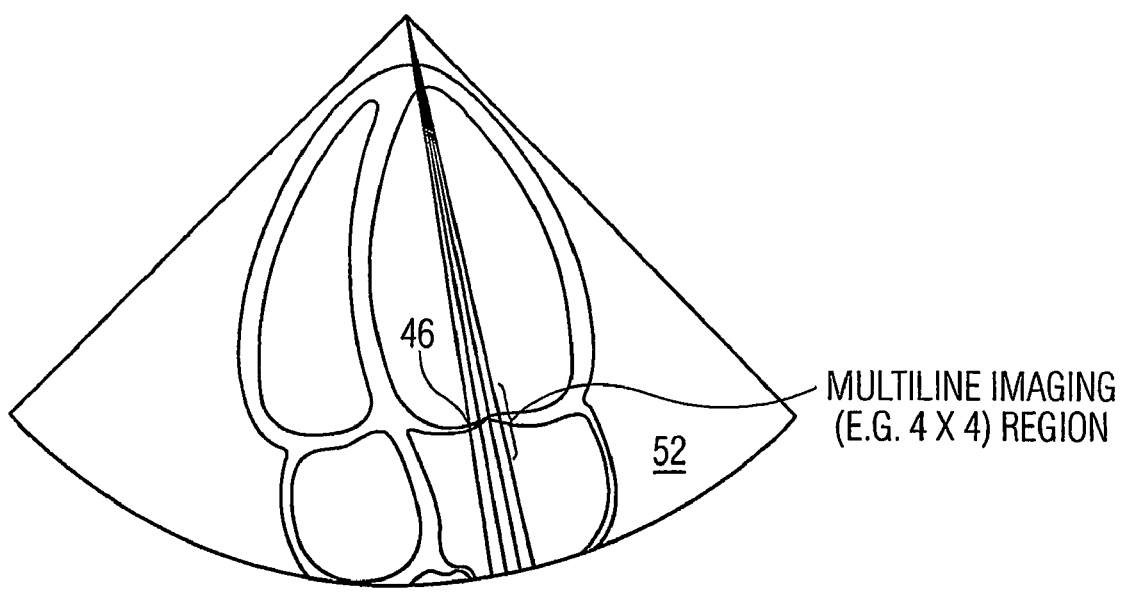
FIG. 5 depicts a volume containing a heart wherein the mitral valve has been automatically detected and imaged with a multi-line scan beam in accordance with the present invention.

In a further embodiment, the acquisition volume for Doppler data can be expanded into a conical zone 52 by the use of multi-line beamforming, as illustrated in FIG. 5. Multi-line beamforming is a technique for receiving (focusing and steering) more than one receive beam from one transmit event (e.g., beam). Such a process is described in U.S. Pat. No. 6,471,650 B2, which is hereby incorporated by reference. In this case, a multi-line bundle (for example, 2×2 or 4×4) covers a finite value of interest around the orifice 46. The acquisition would store the received data in such a manner that the phase information is preserved, for instance the radio frequency data or basebanded IQ data etc., enabling a flexible retrospective review of the entire acquisition volume.

It is understood that the systems, functions, mechanisms, methods, and modules described herein can be implemented in hardware, software, or a combination of hardware and software. They may be implemented by any type of computer system or other apparatus adapted for carrying out the methods described herein. A typical combination of hardware and software could be a general-purpose computer system with a computer program that, when loaded and executed, controls the computer system such that it carries out the methods described herein. Alternatively, a specific use computer, containing specialized hardware for carrying out one or more of the functional tasks of the invention could be utilized. The present invention can also be embedded in a computer program product, which comprises all the features enabling the implementation of the methods and functions described herein, and which—when loaded in a computer system—is able to carry out these methods and functions. Computer program, software program, program, program product, or software, in the present context mean any expression, in any language, code or notation, of a set of instructions intended to cause a system having an information processing capability to perform a particular function either directly or after either or both of the following: (a) conversion to another language, code or notation; and/or (b) reproduction in a different material form.

The foregoing description of the preferred embodiments of the invention has been presented for purposes of illustration and description. They are not intended to be exhaustive or to limit the invention to the precise form disclosed, and obviously many modifications and variations are possible in light of the above teachings. Such modifications and variations that are apparent to a person skilled in the art are intended to be included within the scope of this invention as defined by the accompanying claims.

The invention claimed is:

1. A method of capturing an image using an ultrasound system, comprising:
   directing ultrasound waves from the ultrasound system to a body;
   surveying the image to collect motion data;
   analyzing the motion data to identify a flow in the image, the analyzing comprising segmenting the image into a flow region and a non-flow region;
   scanning a limited region of the image containing the flow with a flow imaging technique;
   distinguishing plaque from clutter when low-level echoes are present; and
   adjusting a gain of an image acquisition system based on whether plaque is present or clutter is present in the image.

2. The method of claim 1, wherein surveying step comprises the step of collecting a sample of color flow data.

3. The method of claim 2, wherein surveying step comprises the step of collecting contour data.

4. The method of claim 1, wherein the analyzing step generates a motion map that identifies flow and non-flow regions.

5. The method of claim 1, wherein the flow imaging technique includes a technique selected from the group consisting of: color flow, time domain correlation, speckle tracking, strain imaging, pulse wave Doppler, and continuous wave Doppler.

6. The method of claim 1, wherein the flow is associated with a valve in a heart.

7. The method of claim 1, wherein the flow indicates a blood vessel.

8. The method of claim 1, wherein the scanning step uses multi-line beamforming.

9. The method of claim 1, wherein the flow is periodically tracked and the limited region of the image containing the flow is automatically adjusted.

10. The method of claim 1, wherein the limited region for acquisition is a region selected from the group consisting of a 3D pie slice, a cube, an arbitrary shape, and a collection of shapes.

11. The method of claim 1, wherein the scanning step includes adjusting a set of acquisition parameters selected from the group consisting of b-mode line densities, colorflow line densities, pulse repetition frequency, and ensemble length.

12. An ultrasound system stored in a non-transitory computer readable medium, comprising:
   a survey system for collecting motion data from a target image;
   an image acquisition system;
   a segmentation system for mapping a region of flow within the image based on the motion data, the segmentation system configured to segment the image into a flow region and a non-flow region;
   a flow acquisition system that automatically limits the collection of flow image data within the image to the region of flow; and
   a plaque/clutter analysis system configured to distinguish between plaque and clutter and to adjust a gain of the image acquisition system based on whether plaque is present or clutter is present.

13. The ultrasound system of claim 12, wherein the motion data comprises color flow data.

14. The ultrasound system of claim 13, wherein the motion data comprises contour data.

15. The ultrasound system of claim 12, wherein the flow acquisition system collects data using an imaging technique selected from the group consisting of: color flow, time domain correlation, speckle tracking, strain imaging, pulse wave Doppler, and continuous wave Doppler.

16. The ultrasound system of claim 12, wherein the flow acquisition system uses multi-line beamforming.

17. The ultrasound system of claim 12, wherein the region of flow is periodically tracked and automatically adjusted.

18. The ultrasound system of claim 12, wherein region of flow is a region selected from the group consisting of a 3D pie slice, a cube, an arbitrary shape, and a collection of shapes.

19. The ultrasound system of claim 12, wherein the flow acquisition system includes a set of acquisition parameters selected from the group consisting of: b-mode line densities, colorflow line densities, pulse repetition frequency, and ensemble length.

* * * * *